United States Patent [19]

Badziong et al.

[11] Patent Number: 5,866,371
[45] Date of Patent: Feb. 2, 1999

[54] PROCESS FOR USING THE YEAST ADH II PROMOTER SYSTEM FOR THE PRODUCTION OF HETEROLOGOUS PROTEINS IN HIGH YIELDS

[75] Inventors: Werner Badziong, Bad Soden; Paul Habermann, Eppstein; Joerg Moeller, Bad Soden; Werner Aretz, Konigstein, all of Germany

[73] Assignee: Hoechst Aktiengesellschaft, Frankfurt, Germany

[21] Appl. No.: 757,439

[22] Filed: Nov. 27, 1996

[30] Foreign Application Priority Data

Nov. 28, 1995 [DE] Germany .......................... 19544233.4

[51] Int. Cl.$^6$ .......................... C12P 21/00; C12P 21/02; C12N 1/19

[52] U.S. Cl. .................. 435/69.2; 435/69.4; 435/69.6; 435/254.21

[58] Field of Search .................. 435/69.1, 69.2, 435/69.4, 69.6, 69.7, 69.9, 252.3, 254.11, 254.2, 254.21, 255.2

[56] References Cited

U.S. PATENT DOCUMENTS

| | | | |
|---|---|---|---|
| 4,668,662 | 5/1987 | Tripier | 514/12 |
| 4,791,100 | 12/1988 | Kramer et al. | 514/12 |
| 5,180,668 | 1/1993 | Crause et al. | 435/69.2 |
| 5,422,249 | 6/1995 | Liersch et al. | 435/69.2 |

FOREIGN PATENT DOCUMENTS

| | | |
|---|---|---|
| 0 158 564 | 10/1985 | European Pat. Off. . |
| 0 158 986 | 10/1985 | European Pat. Off. . |
| 0 168 342 | 1/1986 | European Pat. Off. . |
| 0 171 024 | 2/1986 | European Pat. Off. . |
| 0 193 175 | 9/1986 | European Pat. Off. . |
| 0 200 655 | 11/1986 | European Pat. Off. . |
| 0 209 061 | 1/1987 | European Pat. Off. . |
| 0 324 712 | 7/1989 | European Pat. Off. . |
| 0 347 781 | 12/1989 | European Pat. Off. . |
| 33 42 199 | 5/1984 | Germany . |
| 34 45 517 | 6/1986 | Germany . |

OTHER PUBLICATIONS

Zhang, Yiying et al., "Positional cloning of the mouse obese gene and its human homologue," *Nature*, vol. 372, pp. 425–432, (Dec. 1, 1994).

Hersbach, George J. M. et al., "Biotechnology of Industrial Antibiotics," *Drugs and the Pharmaceutical Sciences*, vol. 22, pp. 45–140 (1984).

Dodt, Johannes et al., "The Complete Covalent Structure of Hirudin," *Biol. Chem. Hoppe–Seyler*, vol. 366, pp. 379–385 (Apr. 1985).

Markwardt, F., "Pharmacology of Hirudin: One hundred years after the first report of the anticoagulant agent in medicinal leeches," *Biomed. Biochim. Acta*, vol. 44, pp. 1007–1013 (1985).

Irani, Meher et al., "Transcription of the ADH2 Gene in *Saccharomyces cerevisiae* Is Limited by Positive Factors That Bind Competitively to Its Intact Promoter Region on Multicopy Plasmids," *Molecular and Cellular Biology*, pp. 1233–1241 (Mar. 1987).

Price, Virginia L. et al., "Expression of Heterologous Proteins in *Saccharomyces cerevisiae* Using the ADH2 Promoter," *Methods in Enzymology*, vol. 185, pp. 308–318 (1990).

Tottrup, Hanne V. et al., "A Process for the Production of Human Proinsulin in *Saccharomyces cerevisiae*," *Biotechnology and Bioengineering*, vol. 35, pp. 339–348 (1990).

Romanos et al., Yeast, vol. 8, pp. 423–488, 1992.

*Primary Examiner*—David Guzo
*Attorney, Agent, or Firm*—Foley & Lardner

[57] ABSTRACT

The invention relates to a novel process for using the yeast ADH II promoter system for the production of heterologous proteins in high yields, for example for preparing hirudins, miniproinsulins, leptins or derivatives thereof.

16 Claims, 6 Drawing Sheets

FIG. IA pADH2IIirkLTY - Hirudin expression vector
Length: 8491

```
   1 GAATTCACCA TTCCTTGCGG CGGCGGTGCT CAACGGCCTC AACCTACTAC
  51 TGGGCTGCTT CCTAATGCAG GAGTCGCATA AGGGAGAGCG TCGACCGATG
 101 CCCTTGAGAG CCTTCAACCC AGTCAGCTCC TTCCGGTGGG CGCGGGGCAT
 151 GACTATCGTC GCCGCACTTA TGACTGTCTT CTTTATCATG CAACTCGTAG
 201 GACAGGTGCC GGCAGCGCTC TGGGTCATTT TCGGCGAGGA CCGCTTTCGC
 251 TGGAGCGCGA CGATGATCGG CCTGTCGCTT GCGGTATTCG GAATCTTGCA
 301 CGCCCTCGCT CAAGCCTTCG TCACTGGTCC CGCCACCAAA CGTTTCGGCG
 351 AGAAGCAGGC CATTATCGCC GGCATGGCGG CCGACGCGCT GGGCTACGTC
 401 TTGCTGGCGT TCGCGACGCG AGGCTGGATG GCCTTCCCCA TTATGATTCT
 451 TCTCGCTTCC GGCGGCATCG GATGCCCGC GTTGCAGGCC ATGCTGTCCA
 501 GGCAGGTAGA TGACGACCAT CAGGGACAGC TTCAAGGATC GCTCGCGGCT
 551 CTTACCAGCC TAACTTCGAT CACTGGACCG CTGATCGTCA CGGCGATTTA
 601 TGCCGCCTCG GCGAGCACAT GGAACGGGTT GGCATGGATT GTAGGCGCCG
 651 CCCTATACCT TGTCTGCCTC CCCGCGTTGC GTCGCGGTGC ATGGAGCCGG
 701 GCCACCTCGA CCTGAATGGA AGCCGGCGGC ACCTCGCTAA CGGATTCACC
 751 ACTCCAAGAA TTGGAGCCAA TCAATTCTTG CGGAGAACTG TGAATGCGCA
 801 AACCAACCCT GGCAGAACA TATCCATCGC GTCCGCCATC TCCAGCAGCC
 851 GCACGCGGCG CATCTCGGGC AGCGTTGGGT CCTGGCCACG GGTGCGCATG
 901 ATCGTGCTCC TGTCGTTGAG GACCCGGCTA GGCTGGCGGG GTTGCCTTAC
 951 TGGTTAGCAG AATGAATCAC CGATACGCGA GCGAACGTGA AGCGACTGCT
1001 GCTGCAAAAC GTCTGCGACC TGAGCAACAA CATGAATGGT CTTCGGTTTC
1051 CGTGTTTCGT AAAGTCTGGA AACGCGGAAG TCAGCGCCCT GCACCATTAT
1101 GTTCCGGATC TGCATCGCAG GATGCTGCTG GCTACCCTGT GGAACACCTA
1151 CATCTGTATT AACGAAGCGC TGGCATTGAC CCTGAGTGAT TTTTCTCTGG
1201 TCCCGCCGCA TCCATACCGC CAGTTGTTTA CCCTCACAAC GTTCCAGTAA
```

FIG. 1B

```
1251 CCGGGCATGT TCATCATCAG TAACCCGTAT CGTGAGCATC CTCTCTCGTT

1301 TCATCGGTAT CATTACCCCC ATGAACAGAA ATTCCCCCTT ACACGGAGGC

1351 ATCAAGTGAC CAAACAGGAA AAAACCGCCC TTAACATGGC CCGCTTTATC

1401 AGAAGCCAGA CATTAACGCT TCTGGAGAAA CTCAACGAGC TGGACGCGGA

1451 TGAACAGGCA GACATCTGTG AATCGCTTCA CGACCACGCT GATGAGCTTT

1501 ACCGCAGCTG CCTCGCGCGT TTCGGTGATG ACGGTGAAAA CCTCTGACAC

1551 ATGCAGCTCC CGGAGACGGT CACAGCTTGT CTGTAAGCGG ATGCCGGGAG

1601 CAGACAAGCC CGTCAGGGCG CGTCAGCGGG TGTTGGCGGG TGTCGGGGCG

1651 CAGCCATGAC CCAGTCACGT AGCGATAGCG GAGTGTATAC TGGCTTAACT

1701 ATGCGGCATC AGAGCAGATT GTACTGAGAG TGCACCATAT GCGGTGTGAA

1751 ATACCGCACA GATGCGTAAG GAGAAAATAC CGCATCAGGC GCTCTTCCGC

1801 TTCCTCGCTC ACTGACTCGC TGCGCTCGGT CGTTCGGCTG CGGCGAGCGG

1851 TATCAGCTCA CTCAAAGGCG GTAATACGGT TATCCACAGA ATCAGGGGAT

1901 AACGCAGGAA AGAACATGTG AGCAAAAGGC CAGCAAAAGG CCAGGAACCG

1951 TAAAAAGGCC GCGTTGCTGG CGTTTTTCCA TAGGCTCCGC CCCCCTGACG

2001 AGCATCACAA AAATCGACGC TCAAGTCAGA GGTGGCGAAA CCCGACAGGA

2051 CTATAAAGAT ACCAGGCGTT TCCCCCTGGA AGCTCCCTCG TGCGCTCTCC

2101 TGTTCCGACC CTGCCGCTTA CCGGATACCT GTCCGCCTTT CTCCCTTCGG

2151 GAAGCGTGGC GCTTTCTCAT AGCTCACGCT GTAGGTATCT CAGTTCGGTG

2201 TAGGTCGTTC GCTCCAAGCT GGGCTGTGTG CACGAACCCC CCGTTCAGCC

2251 CGACCGCTGC GCCTTATCCG GTAACTATCG TCTTGAGTCC AACCCGGTAA

2301 GACACGACTT ATCGCCACTG GCAGCAGCCA CTGGTAACAG GATTAGCAGA

2351 GCGAGGTATG TAGGCGGTGC TACAGAGTTC TTGAAGTGGT GGCCTAACTA

2401 CGGCTACACT AGAAGGACAG TATTTGGTAT CTGCGCTCTG CTGAAGCCAG

2451 TTACCTTCGG AAAAAGAGTT GGTAGCTCTT GATCCGGCAA ACAAACCACC

2501 GCTGGTAGCG GTGGTTTTTT TGTTTGCAAG CAGCAGATTA CGCGCAGAAA

2551 AAAAGGATCT CAAGAAGATC CTTTGATCTT TTCTACGGGG TCTGACGCTC

2601 AGTGGAACGA AAACTCACGT TAAGGGATTT TGGTCATGAG ATTATCAAAA

2651 AGGATCTTCA CCTAGATCCT TTTAAATTAA AAATGAAGTT TTAAATCAAT
```

FIG. IC

```
2701 CTAAAGTATA TATGAGTAAA CTTGGTCTGA CAGTTACCAA TGCTTAATCA
2751 GTGAGGCACC TATCTCAGCG ATCTGTCTAT TTCGTTCATC CATAGTTGCC
2801 TGACTCCCCG TCGTGTAGAT AACTACGATA CGGGAGGGCT TACCATCTGG
2851 CCCCAGTGCT GCAATGATAC CGCGAGACCC ACGCTCACCG GCTCCAGATT
2901 TATCAGCAAT AAACCAGCCA GCCGGAAGGG CCGAGCGCAG AAGTGGTCCT
2951 GCAACTTTAT CCGCCTCCAT CCAGTCTATT AATTGTTGCC GGGAAGCTAG
3001 AGTAAGTAGT TCGCCAGTTA ATAGTTTGCG CAACGTTGTT GCCATTGCTG
3051 CAGGCATCGT GGTGTCACGC TCGTCGTTTG GTATGGCTTC ATTCAGCTCC
3101 GGTTCCCAAC GATCAAGGCG AGTTACATGA TCCCCCATGT TGTGCAAAAA
3151 AGCGGTTAGC TCCTTCGGTC CTCCGATCGT TGTCAGAAGT AAGTTGGCCG
3201 CAGTGTTATC ACTCATGGTT ATGGCAGCAC TGCATAATTC TCTTACTGTC
3251 ATGCCATCCG TAAGATGCTT TTCTGTGACT GGTGAGTACT CAACCAAGTC
3301 ATTCTGAGAA TAGTGTATGC GGCGACCGAG TTGCTCTTGC CCGGCGTCAA
3351 CACGGGATAA TACCGCGCCA CATAGCAGAA CTTTAAAAGT GCTCATCATT
3401 GGAAAACGTT CTTCGGGGCG AAAACTCTCA AGGATCTTAC CGCTGTTGAG
3451 ATCCAGTTCG ATGTAACCCA CTCGTGCACC CAACTGATCT TCAGCATCTT
3501 TTACTTTCAC CAGCGTTTCT GGGTGAGCAA AAACAGGAAG GCAAAATGCC
3551 GCAAAAAAGG GAATAAGGGC GACACGGAAA TGTTGAATAC TCATACTCTT
3601 CCTTTTTCAA TATTATTGAA GCATTTATCA GGGTTATTGT CTCATGAGCG
3651 GATACATATT TGAATGTATT TAGAAAAATA AACAAATAGG GGTTCCGCGC
3701 ACATTTCCCC GAAAAGTGCC ACCTGACGTC TAAGAAACCA TTATTATCAT
3751 GACATTAACC TATAAAAATA GGCGTATCAC GAGGCCCTTT CGTCTTCAAG
3801 AATTAATTCG GTCGAAAAAA GAAAAGGAGA GGGCCAAGAG GGAGGGCATT
3851 GGTGACTATT GAGCACGTGA GTATACGTGA TTAAGCACAC AAAGGCAGCT
3901 TGGAGTATGT CTGTTATTAA TTTCACAGGT AGTTCTGGTC CATTGGTGAA
3951 AGTTTGCGGC TTGCAGAGCA CAGAGGCCGC AGAATGTGCT CTAGATTCCG
4001 ATGCTGACTT GCTGGGTATT ATATGTGTGC CCAATAGAAA GAGAACAATT
4051 GACCCGGTTA TTGCAAGGAA AATTTCAAGT CTTGTAAAAG CATATAAAAA
4101 TAGTTCAGGC ACTCCGAAAT ACTTGGTTGG CGTGTTTCGT AATCAACCTA
```

FIG. 1D

```
4151 AGGAGGATGT TTTGGCTCTG GTCAATGATT ACGGCATTGA TATCGTCCAA
4201 CTGCATGGAG ATGAGTCGTG GCAAGAATAC CAAGAGTTCC TCGGTTTGCC
4251 AGTTATTAAA AGACTCGTAT TTCCAAAAGA CTGCAACATA CTACTCAGTG
4301 CAGCTTCACA GAAACCTCAT TCGTTTATTC CCTTGTTTGA TTCAGAAGCA
4351 GGTGGGACAG GTGAACTTTT GGATTGGAAC TCGATTTCTG ACTGGGTTGG
4401 AAGGCAAGAG AGCCCCGAAA GCTTACATTT TATGTTAGCT GGTGGACTGA
4451 CGCCAGAAAA TGTTGGTGAT GCGCTTAGAT TAAATGGCGT TATTGGTGTT
4501 GATGTAAGCG GAGGTGTGGA GACAAATGGT GTAAAAGACT CTAACAAAAT
4551 AGCAAATTTC GTCAAAAATG CTAAGAAATA GGTTATTACT GAGTAGTATT
4601 TATTTAAGTA TTGTTTGTGC ACTTGCCTGC AGCTTCTCAA TGATATTCGA
4651 ATACGCTTTG AGGAGATACA GCCTAATATC CGACAAACTG TTTTACAGAT
4701 TTACGATCGT ACTTGTTACC CATCATTGAA TTTTGAACAT CCGAACCTGG
4751 GAGTTTTCCC TGAAACAGAT AGTATATTTG AACCTGTATA ATAATATATA
4801 GTCTAGCGCT TTACGGAAGA CAATGTATGT ATTTCGGTTC CTGGAGAAAC
4851 TATTGCATCT ATTGCATAGG TAATCTTGCA CGTCGCATCC CCGGTTCATT
4901 TTCTGCGTTT CCATCTTGCA CTTCAATAGC ATATCTTTGT TAACGAAGCA
4951 TCTGTGCTTC ATTTTGTAGA ACAAAAATGC AACGCGAGAG CGCTAATTTT
5001 TCAAACAAAG AATCTGAGCT GCATTTTTAC AGAACAGAAA TGCAACGCGA
5051 AAGCGCTATT TTACCAACGA AGAATCTGTG CTTCATTTTT GTAAAACAAA
5101 AATGCAACGC GAGAGCGCTA ATTTTTCAAA CAAAGAATCT GAGCTGCATT
5151 TTTACAGAAC AGAAATGCAA CGCGAGAGCG CTATTTTACC AACAAAGAAT
5201 CTATACTTCT TTTTTGTTCT ACAAAAATGC ATCCCGAGAG CGCTATTTTT
5251 CTAACAAAGC ATCTTAGATT ACTTTTTTTC TCCTTTGTGC GCTCTATAAT
5301 GCAGTCTCTT GATAACTTTT TGCACTGTAG GTCCGTTAAG GTTAGAAGAA
5351 GGCTACTTTG GTGTCTATTT TCTCTTCCAT AAAAAAAGCC TGACTCCACT
5401 TCCCGCGTTT ACTGATTACT AGCGAAGCTG CGGGTGCATT TTTTCAAGAT
5451 AAAGGCATCC CCGATTATAT TCTATACCGA TGTGGATTGC GCATACTTTG
5501 TGAACAGAAA GTGATAGCGT TGATGATTCT TCATTGGTCA GAAAATTATG
5551 AACGGTTTCT TCTATTTTGT CTCTATATAC TACGTATAGG AAATGTTTAC
```

FIG. IE

```
5601 ATTTTCGTAT TGTTTTCGAT TCACTCTATG AATAGTTCTT ACTACAATTT
5651 TTTTGTCTAA AGAGTAATAC TAGAGATAAA CATAAAAAAT GTAGAGGTCG
5701 AGTTTAGATG CAAGTTCAAG GAGCGAAAGG TGGATGGGTA GGTTATATAG
5751 GGATATAGCA CAGAGATATA TAGCAAAGAG ATACTTTTGA GCAATGTTTG
5801 TGGAAGCGGT ATTCGCAATA TTTTAGTAGC TCGTTACAGT CCGGTGCGTT
5851 TTTGGTTTTT TGAAAGTGCG TCTTCAGAGC GCTTTTGGTT TTCAAAAGCG
5901 CTCTGAAGTT CCTATACTTT CTAGAGAATA GGAACTTCGG AATAGGAACT
5951 TCAAAGCGTT TCCGAAAACG AGCGCTTCCG AAAATGCAAC GCGAGCTGCG
6001 CACATACAGC TCACTGTTCA CGTCGCACCT ATATCTGCGT GTTGCCTGTA
6051 TATATATATA CATGAGAAGA ACGGCATAGT GCGTGTTTAT GCTTAAATGC
6101 GTACTTATAT GCGTCTATTT ATGTAGGATG AAAGGTAGTC TAGTACCTCC
6151 TGTGATATTA TCCCATTCCA TGCGGGGTAT CGTATGCTTC CTTCAGCACT
6201 ACCCTTTAGC TGTTCTATAT GCTGCCACTC CTCAATTGGA TTAGTCTCAT
6251 CCTTCAATGC TATCATTTCC TTTGATATTG GATCATATGC ATAGTACCGA
6301 GAAACTAGTG CGAAGTAGTG ATCAGGTATT GCTGTTATCT GATGAGTATA
6351 CGTTGTCCTG GCCACGGCAG AAGCACGCTT ATCGCTCCAA TTTCCCACAA
6401 CATTAGTCAA CTCCGTTAGG CCCTTCATTG AAAGAAATGA GGTCATCAAA
6451 TGTCTTCCAA TGTGAGATTT TGGGCCATTT TTTATAGCAA AGATTGAATA
6501 AGGCGCATTT TTCTTCAAGG GGGGGGGGGG GGGGGGGGGG TTACTTAACC
6551 AATCTACATA GATACTATAT TTAACATTCA ACATAATAAT AAATATTTTG
6601 GGATAAATAA GTGAAACCAT TTTAGAGCCC CTAGGGCTTA CAAAAAGAAT
6651 CATAAAAGAT CCATATTTAT AGTTTTAAGA TTAAGAATAA TAGTTACAAT
6701 AGGTAGCAAA CCATACATTC AACAATAAAT ATAAAATTTA AATATTTAAA
6751 TAAATAGAAG GGGTACGAGG GGGCCATGGA CGAGCTCTAT TACTGAAGGT
6801 ATTCCTCAGG GATCTCTTCG AAGTCGCCGT CGTTATGAGA CTGCGGTTTC
6851 GGGGTACCTT CGCCAGTAAC GCACTGGTTC TTTTCACCGT CGGATCCAAG
6901 GATGCATTTG TTACCCTGGC CGCAAACGTT AGATCCTTCG CACAGGCACA
6951 GGTTCTGACC AGATTCAGTG CAGTCAGTAT ACGTAAGTCT TTTATCCAAA
7001 GGTACCCCTT CTTCTTTAGC AGCAATGCTG GCAATAGTAG TATTTATAAA
```

FIG. 1F

```
7051 CAATAACCCG TTATTTGTGC TGTTGGAAAA TGGCAAAACA GCAACATCGA
7101 AATCCCCTTC TAAATCTGAG TAACCGATGA CAGCTTCAGC CGGAATTTGT
7151 GCCGTTTCAT CTTCTGTTGT AGTGTTGACT GGAGCAGCTA ATGCGGAGGA
7201 TGCTGCGAAT AAAACTGCAG TAAAAATTGA AGGAAATCTC ATCGTGAGGT
7251 CGAGCTTGGT GTATTACGAT ATAGTTAATA GTTGATAGTT GATTGTATGC
7301 TTTTTGTAGC TTGATATTCT ATTTACCAAG AAGAAACAAG AAGTGATAAA
7351 AACAACAAGA GAGCAGTAGT AAGAGTATTT CAGTGTGAAA AAAGTCGCTA
7401 CTGGCACTCT ATTTATATGT GATAGGCATG CTATAGCTTT ACCAAAAAGT
7451 GAACCCCATT TCTATGCTCT CCTCTGCCTT TTTTTTTTTT TTTTTTTTCA
7501 TTCTCTCAAT CTGAAATTCT CTTATTTCTC CAACTTATAA GTTGGAGATG
7551 CCCGGTGTTC CGGCAGAGGA GATCAGTCTC GTGAAGTGGA TGGTTTCCCG
7601 CCTGCGGGCA AAACGTCATA ACATTTTTAT GAGCGAAAGC CGTTAATGAA
7651 GACAAAATCC CTTAATTAAA ACATTAGAAT GGTGATTAGA AAGGCAGGAT
7701 TAATCAGTTA CACAGGCTGT AACCGGAGAG ACGGATCATA AGGCAATTTT
7751 TAGATAAGAC TGGTTAGAGT TCTTGGCATC AGAAAATTTG AGAAACGATT
7801 TTTCCGTTTG TTTGCCCCTA CGTTTTGCCC CTTTGATCAA ACTATCAGTT
7851 AAGATATTAA TTTTTTTGAG AAAACGATTC TTTGATTAGT CTCTTCAAAC
7901 AAACAATGAG CTCTGAAGAC GAATTGGGAA GTATCGGTAC TGTGTTTCCC
7951 GGAAGTCCCA TAGATAAGAG CATTGGGAGT ATTCTCCACA ATTTGATGAA
8001 GAAGTGGAGA CTTTGCTGGA AGATAGCTTC ACGTGGAACA TTCCTGACTG
8051 GAACGAGTTA ACAAACCCGA ATACAATTC GCCCAGGTTT AGAATTGGTG
8101 ATTTCGAATG GGACATTCTA TTATTCCCTC AGGGAAACCA TAATAAAGGT
8151 GTTGCGGTAT ATCTGGAACC TCATCCGGAA GAAAAATTAG ATGAGACTAC
8201 GGGAGAGATG GTGCCAGTTG ATCCGGACTG GTATTGTTGT GCTCAGTTTG
8251 CCATTGGTAT ATCTAGACCT GGTAATGGTG ACACCATCAA TTTAATTAAC
8301 AAATCGCATC ACCGATTCAA CGCTCTAGAT ACAGACTGGG GATTTGCAAA
8351 TTTGATAGAT TTGAACAACT TGAAACATCC CTCAAAAGGA AGACCGCTTT
8401 CGTTCTTAAA CGAAGGGACC TTGAACATAA CAGCGTATGT GCGCATATTG
8451 AAGGATCTCT ACTTGTCAAA TACCTTTAAA TCTTATCAAT A
```

PROCESS FOR USING THE YEAST ADH II PROMOTER SYSTEM FOR THE PRODUCTION OF HETEROLOGOUS PROTEINS IN HIGH YIELDS

BACKGROUND OF THE INVENTION

The polypeptide hirudin, which was originally isolated from the leech *Hirudo medicinalis*, is a highly specific thrombin inhibitor possessing a broad therapeutic potential (F. Markwardt, Biomed. Biochim. Acta 44 (1985) 1007–1013). However, it is only possible to prepare the quantities which are required by the recombinant route using transformed microorganisms. In this context, it has been found that the yeast *Saccharomyces cerevisiae* is suitable as a host organism for producing hirudin which is correctly folded and fully active (EP A1 168 342, EP A1 200 655).

The gene for the alcohol dehydrogenase isoenzyme II (ADH II) is strictly regulated in yeast cells. The product of the ADH II gene is not found when fermentable carbon sources, such as glucose, are added to the fermentation medium. ADH II catalyzes the dehydration of ethanol ($C_2H_5OH$) to acetaldehyde ($CH_3COH$). However, conditions for inducing the ADH II promoter can be achieved in simple aerobic batch processes, in shaking flasks or in fermenters, which are started, for example, using a glucose concentration of 4%. When growth takes place on glucose, the so-called "Crabtree" effect results in ethanol being formed initially with the aid of the enzyme ADH I, with the ethanol in turn being used as an additional carbon source once the glucose has been completely consumed. After the glucose has been broken down, the ethanol-degrading enzyme ADH II is induced and the expression of the ADH II gene product begins. If the expression of a gene encoding a heterologous protein is under control of the ADH II promoter, expression of the heterologous protein will begin once the glucose has been metabolized.

As a rule, such batch fermentations do not provide the high yield which is sought for industrial applications. In general, industrial applications require a high yield in a short period of time. What is wanted is the separation of the fermentation into a growth phase and a production phase, as is achieved in classical antibiotic fermentations, for example, by means of a limited fed-batch procedure (also known in the art as feed-batch), in which, after a certain cell density has been established, a carbon source is then fed in a growth-limiting manner in order to form the product (e.g. the secondary metabolite penicillin) at high yield under optimal physiological conditions See Hersbach et al.: The Penicillins: Properties, Biosynthesis and Fermentation, in: Biotechnology of Industrial Antibiotics, pp. 45–140, Ed. E. J. Vandamme, Marcel Dekker, New York, 1984.

Because of the way it is regulated, the ADH II promoter system has been used for the preparation of recombinant proteins in the bakers yeast *Saccharomyces cerevisiae*. See Price et al.: Methods of Enzymology, Vol. 185, 308–318, 1990, which is hereby incorporated by reference. The fermentation system used by Price depends on the growth of the yeast cells and on the natural elimination of glucose as a carbon source. In the absence of glucose, product formation is switched on and continues until the end of the fermentation. However, the yield of product appears to be less than was hoped.

Tøttrup et al. (Biotechnol. Bioeng., 35, 339–348, 1990) describe a modified fermentation procedure for the intracellular production of a human insulin fusion protein, which procedure involves feeding with glucose followed by feeding with ethanol in order to ensure optimal induction of the system. This group used a hybrid promoter, which consisted of the ADH II promoter ligated to the glyceraldehyde-3-phosphate dehydrogenase promoter. These workers succeeded in almost doubling the volume-related product yield (grams protein/liter), as compared with a batch process, by means of continually feeding glucose at a constant rate over the entire fermentation period. A further doubling was finally achieved by means of replacing the glucose feed, from a particular time point onward, with an ethanol feed. It was concluded from this result that even when there is no glucose, or very low glucose concentrations of less than 20 mg/l, in the culture broth, the hybrid promoter is still partially repressed by glucose or a metabolite of glycolysis. Complete induction was only achieved by adding ethanol.

Thus, it would be useful to have a high-yield process for producing heterologous protein in yeast using the ADH II promoter system. As used herein an "ADH II promoter system" means that the expression of a heterologous gene is under the control of the ADH II promoter.

SUMMARY OF THE INVENTION

The present application is directed to a biotechnology invention.

It is an object of the invention to provide a process for producing a heterologous protein by fermentation of transformed yeast, said process comprising:

a) inoculating a main culture medium with a preliminary culture medium, wherein said preliminary medium comprises yeast which contain an expression vector comprising a gene encoding said heterologous protein and an ADH II promoter, wherein the expression of said gene is under the control of the yeast ADH II promoter;

b) immediately following the inoculation of step (a), adding 0.7 to 1.4 grams of glucose/liter of culture volume/hour to said main medium, wherein said glucose is added continuously at a constant rate; and c) isolating said heterologous protein from the fermentation culture;

wherein said fermentation is carried out for a time sufficient to produce the desired level of heterologous protein, and wherein said yeast are cultured under aerobic conditions.

It is a further embodiment of the invention to provide such a process where the fermentation is carried out for approximately two days. In other embodiments of the invention, there are provided processes for production of heterologous protein in yeast wherein the glucose concentration is from about 0.7 to about 1.4 grams/liter of culture volume/hour. In a further embodiment, the glucose concentration is from 0.9 to 1.3 grams/liter of culture volume/hour. In still further embodiments, the glucose concentration is from about 0.9 to about 1.3 grams/liter of culture volume/hour, or 1.1 grams/liter of culture volume/hour or about 1.1 grams/liter of culture volume/hour.

In another embodiment of the invention, a process is provided where the compositions of the preliminary culture medium and the main culture medium are equivalent with the exception that the preliminary medium contains 1% glucose. In a further embodiment, the glucose in this preliminary culture medium has been almost completely consumed at the time of the inoculation.

In another embodiment of the invention, the aerobic conditions in a process of the invention are maintained by maintaining an oxygen partial pressure of at least 20% saturation.

In yet another embodiment of the invention, the main medium employed in a process according to the invention contains one or more complex constituent selected from the group consisting of cornsteep, soybean meal and yeast extract.

Various types of yeast may be used in a process according to the invention. These yeasts include, but are not limited to *Saccharomyces cerevisiae* (including *Saccharomyces cerevisiae* strain Y79), and *Kluyveromyces lactis*.

The skilled artisan will recognize that any heterologous protein can be produced using a process according to the invention. These heterologous proteins include, but are not limited to, a hirudin, a miniproinsulin, a leptin, a hirudin derivative, a miniproinsulin derivative, and a leptin derivative. These proteins further include, but are not limited to, a fusion protein comprising a protein selected from the group consisting of a hirudin, a miniproinsulin, a leptin, a hirudin derivative, a miniproinsulin derivative, and a leptin derivative.

BRIEF DESCRIPTION OF THE DRAWINGS

FIG. 1 shows the nucleotide sequence for the plasmid-pADHIIHirkLTY (SEQ ID NO:1), which contains the hirudin gene fragment from plasmid pαfHir inserted into the pαADHII plasmid.

DETAILED DESCRIPTION OF THE INVENTION

The invention relates to a novel process for using the yeast ADH II promoter system for the production of heterologous proteins in high yields.

As used herein, a "hirudin" means a peptide-like thrombin inhibitor which is derived from the known isohirudins of the species *Hirudo medicinalis* and which exhibits essential structural features of these isohirudins, in particular the characteristic linking of the three disulfide bridges. J. Dodt et al., Biol. Chem. Hoppe-Seyler 366 (1985) 379–385. Cf. EP A1 158 564, EPA1 168 342, DE 34 45 517, EP A2 193 175, EP A1 200 655, EP A1 158 986, EP A1 209 061, DE 33 42 199, EP A1 171 024).

As used herein, "essential structural features" of an isohirudin is used to mean features that are necessary for the biological function of isohirudin and which are common to all isohirudins. In general, these features are conserved stretches of amino acids with (1) similar or essentially identical three-dimensional structure and (2) similar or essentially identical function. As used herein, "derivatives of isohirudins" is used to mean any protein, derived from hirudin, which exhibits the biological activity of hirudin. These derivatives may be made using genetic engineering techniques that are well known to the skilled artisan, such as the introduction of mutations, deletions, insertions into a nucleotide sequence for an isohirudin so as to produce a modified protein with the biological properties of hirudin. These derivatives may be made using other genetic engineering techniques that are well known to the skilled artisan, such as the production of fusion proteins, chemical or enzymatic generation of hirudin fragments, or chemical modification of hirudin, so as to produce a modified protein with the biological properties of hirudin.

In particular, among these, a hirudin as described in EP A1 171 024, EP A1 158 986 and EP A1 209 061, all of which are incorporated by reference, is an acceptable hirudin in accordance with the invention. Such hirudins can have a range of specific activities. Advantageously, the specific activity of a hirudin produced according to the invention can be at least about 10,000 ATU/mg and advantageously at least 10,000 ATU/mg (anti-thrombin units/mg).

If the expression system described in the article by Price et al. is used for preparing the hirudin gene product described in European Patent Specification 0 324 712 B1, the specific, biomass-based product yield (grams heterologous protein/grams recombinant yeast) decreases as a result of adding ethanol, continuously or discontinuously, since an increased cell growth was not accompanied by increased product titer. See Example 1 below.

The direct addition of ethanol was also investigated on a laboratory scale. First, a culture was started with glucose as the energy source. As the glucose became depleted, ethanol was produced ("Crabtree effect"). At this point in time, additional ethanol was added to the medium. While the additional supplementation of a batch culture with ethanol during growth on ethanol increased the biomass, it did not lead to any increase in product concentration as compared with the culture without supplementation.

Similarly, laboratory cultures which were grown using ethanol as the sole carbon source did not, within the limits of measurement accuracy, result in specific yields (based on the optical density or on the biomass) which were higher than those of a comparison culture using glucose. See Example 2. From this it appears that ethanol on its own is not an inducer of ADH II.

In addition, an attempt to generate derepressed growth, and to avoid ethanol formation due to the Crabtree effect, did not increase product yield. In this regard, regulated, model-assisted glucose feeding ("following up," i.e. increasing, the feeding rate in accordance with the increasing cell density), was followed by inducing expression more powerfully by means of a pulse addition of glucose with a subsequent high level of ethanol formation as a consequence of the Crabtree effect. This method did not increase product yield.

Surprisingly, a fermentation method which is simple and self-regulating and which can be carried out on an industrial scale has now been found for using the yeast ADH II promoter system for the production of heterologous proteins in high yields. This process comprises continuously metering ("adding") glucose, as the carbon source, into a fermentation culture (main culture) in which no glucose was initially present. During the course of the culture, various phases are passed through in such a manner that optimal induction and product formation are achieved. In the light of the state of the art, for example Price et al., supra, such an induction of heterologous gene expression in yeast using the ADH II promoter system is quite remarkable since Price et al. indicate that the ADH II promoter is only derepressed after there has been a marked depletion of glucose.

Using a process according to the invention, optimal product yield coupled with high productivity is achieved when a small quantity of glucose is fed in continuously at a constant rate directly after the main culture has been inoculated with a preliminary culture containing transformed yeast. As used herein, "main medium" is used to mean the culture medium used for large-scale culturing of bacteria. Typically, the main medium culture volume will be above about 1000 liters, although the skilled artisan will recognize that other suitable volumes may be employed. "Preliminary medium" is used to mean the cuture medium used for the preliminary, or initial, culturing of the yeast. Typically, the main medium used in the invention will have the same composition, with the exception that the preliminary culture medium contains 1% glucose, but glucose is added continuously to the main medium throughout the fermentation. Typically, about 1.1 grams of glucose per liter of culture volume is added continuously to the main medium. The increase in volume of the culture due to the feeding-in can lead to a lowering, by up to 25%, of the actual glucose feeding-in rate by the time the culture has ended. At first, glucose is present in excess for the low cell population. This excess glucose represses the ADH II promoter and ethanol is formed as a consequence of the Crabtree effect. From a particular time onward, the cell density is so high that glucose no longer suffices as sole carbon source and mixed growth on glucose and ethanol takes place. After the ethanol which was primarily formed has been consumed and further growth is limited by the depletion or total absence of glucose, the ADH II promoter is switched on and product formation begins. In this way, the product yield can be approximately tripled as compared with the batch process.

Thus, in one embodiment the invention relates to a process for the production ("biotechnological fermentation") of heterologous proteins in yeast in which a main culture is inoculated with a preliminary culture of a yeast strain which can express the heterologous protein; immediately after the inoculation a small quantity of glucose, e.g. 0.7–1.4, preferably 0.9–1.3, and very particularly preferably 1.1, g of glucose/l of culture volume/hour is supplied continuously at a constant rate, the fermentation is terminated after 2 days and, finally, the heterologous protein is isolated from the fermentation culture. Aerobic culture conditions are ensured during the whole of the fermentation by not allowing the oxygen partial pressure to fall below 20% saturation. Other suitable glucose concentrations according to the invention include about 0.7 to about 1.4 grams of glucose/liter of culture volume/hour, about 0.9 to 1.3 grams of glucose/liter of culture volume/hour and 1.1 grams of glucose/liter of culture volume/hour.

The skilled artisan will recognize that there are many culture media suitable for yeast fermentation. Such media include, but are not limited to, media described in Ausubel, et al., eds. CURRENT PROTOCOLS IN MOLECULAR BIOLOGY pp. 13.1.1–13.1.7 (John Wiley & Sons, 1995). For the processes according to the invention, the level of carbon source in the culture medium must be controlled. Typical carbon sources are glucose and ethanol. As indicated above, various medium glucose concentrations are suitable for carrying out the process of the invention. Thus in one embodiment, the medium will comprise one or more complex constituents, but will not contain glucose or other carbon sources, such as sucrose. Appropriate carbon sources will be added when appropriate. In addition, the culture medium used for fermentation will generally be free of ethanol when fermentation is started.

The skilled artisan will recognize that the process of the invention can be carried out until the desired level of heterologous protein has been produced. The process of the invention may be carried out for approximately two days. The skilled artisan will recognize that the process may be carried out for more or less time, depending on the specific experimental conditions employed to produce heterologous protein. In one embodiment, the process of the invention is carried out until the level of heterologous protein production is constant (i.e. the amount of heterologous protein does not further increase with longer times).

In another embodiment, the invention relates to the process described above, in which the media of the preliminary culture and the main culture are equivalent apart from an addition of 1% glucose to the preliminary culture medium, which addition has preferably been almost completely consumed at the time of inoculation of the main culture, and contain one or more complex constituents, for example cornsteep, soybean meal or yeast extract. As used herein, "almost completely consumed" denotes a glucose concentration of less than 100 mg/liter or less than about 100 mg/liter. As used herein, "complex constituents" is used to mean constituents such as cornsteep, soybean meal or yeast extract. Other such constituents are well known to those of skill in the art. The skilled artisan will recognize that such constituents contain a variety of components, some of which are not precisely defined.

The yeast strains used in said processes can be *Saccharomyces cerevisiae,* preferably Y79 (see EP 0 324 712) or *Kluyveromyces lactis* strains. The skilled artisan will recognize that other yeast strains, such as other strains of Saccharomyces or Kluyveromuces, may be used to carry out a process according to the invention.

The heterologous proteins which can be prepared in accordance with the process can be, for example, a hirudin, a miniproinsulin (as described, for example, in EP 0 347 781), a leptin (e.g. obese gene products as described in Zhang et al., Nature 372:425–32, 1994) or a derivative of the previously mentioned proteins or fusion proteins which contain one of the previously mentioned proteins and/or derivatives thereof. In this context, the term derivatives denotes, inter alia, functional, i.e. biologically active, fragments of the starting proteins or mutants possessing novel, in particular advantageous, biological properties. For example a derivative would possess the same biological activity as the native protein, but desirable properties such as prolonged half life (for example in blood), and altered pharmacological action profile. Such a profile may be advantageously delayed, prolonged or shortened, depending on the protein and treatment regimen used. The skilled artisan will recognize that a biologically active peptide fragment may possess one or more of the functional activities of the complete peptide.

The skilled artisan will also recognize that any heterologous protein can be expressed using a process according the invention by using the appropriate nucleotide sequence in a vector according the invention.

Techniques for producing fusion proteins are well known in the art. See, for example, EP 0489 780, hereby incorporated by reference.

The following examples are provided to illustrate the invention, but do not limit the scope of the claimed invention.

EXAMPLE 1

Preparation of the Expression Vector for the Recombinant Production of Hirudin in Yeast This example describes the expression system which has been used for developing the process of the claimed invention.

The vector pα ADH 2 (see FIG. 2A in Price et al., supra, which is hereby incorporated by reference) contains, adjacent to the Spe I restriction enzyme cleavage site in the direction of the 3' end of the cDNA, a recognition site for the enzyme Nco I which is unique for the plasmid. After the DNA of the vector pα ADH 2 was reacted with Kpn I and Nco I, two DNA fragments were then obtained which are separated from each other by gel electrophoresis. The larger of the two fragments was isolated and reacted, in a T4 ligase reaction, with a Kpn I/Nco I hirudin fragment which was isolated from the plasmid Pαf Hir 17 (See EP 0 324 712 B1, which is hereby incorporated by reference) by partial digestion with the enzyme Kpn I and complete digestion with the enzyme Nco I. The complete nucleotide sequence of the resulting plasmid pADH2HirkLTY (SEQ ID NO:1), which contains the hirudin gene fragment from pαf Hir inserted into pαADHII is shown in FIG. 1.

Commercially obtainable competent *E.coli* K12 cells of the strain HB101 were transformed with the ligation mixture and the transformation culture was plated out on Na agar plates which contain 25 mg/l ampicillin. The plates were incubated at 37° C. overnight and, on the following morning, individual colonies were picked from the plates and used to start overnight cultures. Plasmid DNA was in each case isolated from the cells of the cultures and examined by means of restriction analysis. Correct plasmid DNA, which contains the hirudin gene incorporated in the desired manner, was used to transform the *Saccharomyces cerevisiae* strain Y79 as described in EP 0 324 712 B1, which is hereby incorporated by reference.

EXAMPLE 2

Comparison of Laboratory Cultures for the Recombinant Preparation of Hirudin in Yeast Using Different Carbon Sources Different carbon sources were investigated in a laboratory fermenter under otherwise identical conditions. The composition of the medium for the preliminary and main stages is as follows:

1% yeast extract
2% peptone
    carbon source (in each case the same quantity based on the carbon content)
80 mg/l adenine
80 mg/l uracil
pH=5.0

The main culture was inoculated with an inoculum equal in volume to 2% of the main medium and incubated for 48 hours. The cell concentration in the inoculum was from about $3 \times 10^7$ to about $1 \times 10^8$ cells/ml.

The following results were obtained when ethanol and glucose were used as carbon sources:

| Carbon source | Hirudin concentration [%] | Optical density $A_{578\ nm}$ [%] |
| --- | --- | --- |
| 2% glucose | 100 | 100 |
| 1.54% ethanol | 83 | 71 |

The values given in this table are relative. Identical culture volumes were used for each carbon source tested. The hirudin concentration and optical density of the 2% glucose medium at 48 hours were set at 100%. Thus, the table shows that using ethanol resulted in a lower hirudin concentration (83% of the 2% glucose level) and a lower optical density (71% of the 2% glucose level).

EXAMPLE 3

Comparison of the Recombinant Preparation of Hirudin in Yeast by Fermenting With or Without Glucose Feeding a) Fermentation With Glucose Feeding (Fed-Batch Process)

1600 liters of culture medium, which comprises one or more complex constituents, for example cornsteep, soybean meal, yeast extract, etc., without glucose or other carbon sources, such as sucrose, being added, were sterilized at 121° C. for 20 minutes in a fermenter having a total volume of 3600 l.

After it was cooled down, the medium was inoculated with approx. 200 l of a preliminary culture which had been grown for approximately 12 hours (optical density $A_{540nm}$= 3.5±0.5) and which contained only very low residual quantities of glucose. In other words, the glucose was almost completely consumed and was hence present at less than 100 mg/l. The medium of the preliminary culture was equivalent to that of the main culture except that 1% glucose had been added to the preliminary medium before the yeast was grown in this medium for approximately 12 hours.

Immediately after the main stage was inoculated, 2 kg of glucose were metered in (i.e., "added") per hour, in the form of a 20% aqueous solution of glucose at a uniform rate until the end of the fermentation. The glucose was added via a device for ensuring continuous sterilization. The skilled artisan will recognize that such devices are well known in the art. Examples of such devices include a flow through heat exchanger and a continuous flow through sterilizer.

Aerobic conditions must be ensured during the fermentation; an oxygen partial pressure of $pO_2$ greater than or equal to 20% has to be maintained. Accordingly, an oxygen partial pressure of greater than or equal to 20% was maintained during the fermentation in this example.

After 48±2 hours, the fermentation was complete and was terminated by adding 0.225±0.025% benzalkonium chloride, e.g. 0.45±0.05% ®Dodigen 226 (a 50% solution of a mixture of alkyldimethylbenzylammonium chlorides in water) to the culture medium. Completion of fermentation was determined by measuring the concentration of hirudin in the medium, using HPLC. After approximately 48 hours, the level of hirudin remained relatively constant.

The final volume (medium+condensate+preliminary culture+metered-in glucose solution−water loss due to gassing) was 2300±50 l.

Following this, the medium can be worked up for isolation of hirudin from the culture broth, using procedures that are well known to the skilled artisan. See, for example, U.S. Pat. No. 5,180,668 hereby incorporated by reference.

b) Batch Process

The batch process is equivalent to the fed-batch process described in Example 3a) with the following exceptions:

Prior to inoculation, the medium contained 4% glucose in addition to the complex constituents.

No further metering-in of glucose took place.

The final volume was only approx. 1800±50 l.

c) Comparison of the Results

| Process | Hirudin concentration [%] | Hirudin quantity [%] |
| --- | --- | --- |
| Batch process | 100 | 100 |
| Fed-batch process | 228 | 291 |

The numbers in this table are relative levels. The final hirudin concentration and quantity using the batch process were set at 100%. The fed-batch process yielded relatively higher hirudin concentration and quantity.

Priority application 19544233.4 (Federal Republic of Germany), filed Nov. 28, 1995, including the specification, drawings, claims and abstract, is hereby incorporated by reference.

We claim:

1. A process for producing a heterologous protein by fermentation of transformed yeast, said process comprising:
   a) inoculating a main culture medium with a preliminary culture medium, wherein said preliminary medium comprises yeast which contain an expression vector comprising a gene encoding said heterologous protein and an ADH II promoter, wherein the expression of said gene is only under the control of the yeast ADH II promoter;
   b) immediately following the inoculation of step (a), adding 0.7 to 1.4 grams of glucose/liter of culture volume/hour to said main medium, wherein said glucose is added continuously at a constant rate; wherein ethanol is formed by said yeast as a result of the Crabtree effect; and
   c) isolating said heterologous protein from the fermentation culture;
   wherein the production of said protein is initiated after (i) the ethanol that was formed in said main medium has been metabolized by said yeast, and (ii) after growth of said yeast is limited by depletion of glucose by said yeast;
   and wherein said depletion of glucose occurs when the cell density of said yeast is sufficiently high that said continuous addition of glucose is not sufficient to sustain growth of said yeast.

2. The process according to claim 1, wherein said fermentation is carried out for approximately two days.

3. The process according to claim 1, wherein glucose is added at a rate of from 0.9 to 1.3 grams/liter of culture volume/hour.

4. The process according to claim 1, wherein glucose is added at a rate of from about 0.9 to about 1.3 grams/liter of culture volume/hour.

5. The process according to claim 1, wherein glucose is added at a rate of 1.1 grams/liter of culture volume/hour.

6. The process according to claim 1, wherein glucose is added at a rate of about 1.1 grams/liter of culture volume/hour.

7. The process according to claim 1, wherein the compositions of the preliminary culture medium and the main culture medium are equivalent with the exception that the preliminary medium contains 1% glucose.

8. The process according to claim 1, wherein aerobic culture conditions are maintained by maintaining an oxygen partial pressure of at least 20% saturation.

9. The process according to claim 1, wherein said main medium contains one or more complex constituents selected from the group consisting of cornsteep, soybean meal and yeast extract.

10. The process according to claim 1, wherein said yeast is *Saccharomyces cerevisiae*.

11. The process according to claim 1, wherein said yeast is *Kluyveromyces lactis* strain.

12. The process according to claim 1, wherein said heterologous protein is selected from the group consisting of a hirudin, a miniproinsulin, a leptin, a hirudin derivative, a miniproinsulin derivative, and a leptin derivative.

13. The process according to claim 1, wherein said heterologous protein is a fusion protein comprising a protein selected from the group consisting of a hirudin, a miniproinsulin, a leptin, a hirudin derivative, a miniproinsulin derivative, and a leptin derivative.

14. The process according to claim 1, wherein exogenous ethanol is not added to said main medium or said preliminary medium.

15. The process according to claim 7, wherein said glucose in said preliminary culture medium has been almost completely consumed at the time of the inoculation.

16. The process according to claim 15, wherein said yeast is *Saccharomyces cerevisiae* strain Y79.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 8491 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GAATTCACCA  TTCCTTGCGG  CGGCGGTGCT  CAACGGCCTC  AACCTACTAC  TGGGCTGCTT      60

CCTAATGCAG  GAGTCGCATA  AGGGAGAGCG  TCGACCGATG  CCCTTGAGAG  CCTTCAACCC     120

AGTCAGCTCC  TTCCGGTGGG  CGCGGGGCAT  GACTATCGTC  GCCGCACTTA  TGACTGTCTT     180

CTTTATCATG  CAACTCGTAG  GACAGGTGCC  GGCAGCGCTC  TGGGTCATTT  TCGGCGAGGA     240

CCGCTTTCGC  TGGAGCGCGA  CGATGATCGG  CCTGTCGCTT  GCGGTATTCG  GAATCTTGCA     300

CGCCCTCGCT  CAAGCCTTCG  TCACTGGTCC  CGCCACCAAA  CGTTTCGGCG  AGAAGCAGGC     360

CATTATCGCC  GGCATGGCGG  CCGACGCGCT  GGGCTACGTC  TTGCTGGCGT  TCGCGACGCG     420

AGGCTGGATG  GCCTTCCCCA  TTATGATTCT  TCTCGCTTCC  GGCGGCATCG  GATGCCCGC      480

GTTGCAGGCC  ATGCTGTCCA  GGCAGGTAGA  TGACGACCAT  CAGGGACAGC  TTCAAGGATC     540

GCTCGCGGCT  CTTACCAGCC  TAACTTCGAT  CACTGGACCG  CTGATCGTCA  CGGCGATTTA     600

TGCCGCCTCG  GCGAGCACAT  GGAACGGGTT  GGCATGGATT  GTAGGCGCCG  CCCTATACCT     660

TGTCTGCCTC  CCCGCGTTGC  GTCGCGGTGC  ATGGAGCCGG  GCCACCTCGA  CCTGAATGGA     720

AGCCGGCGGC  ACCTCGCTAA  CGGATTCACC  ACTCCAAGAA  TTGGAGCCAA  TCAATTCTTG     780

CGGAGAACTG  TGAATGCGCA  AACCAACCCT  TGGCAGAACA  TATCCATCGC  GTCCGCCATC     840

TCCAGCAGCC  GCACGCGGCG  CATCTCGGGC  AGCGTTGGGT  CCTGGCACG   GGTGCGCATG     900

ATCGTGCTCC  TGTCGTTGAG  GACCCGGCTA  GGCTGGCGGG  GTTGCCTTAC  TGGTTAGCAG     960

AATGAATCAC  CGATACGCGA  GCGAACGTGA  AGCGACTGCT  GCTGCAAAAC  GTCTGCGACC    1020

TGAGCAACAA  CATGAATGGT  CTTCGGTTTC  CGTGTTTCGT  AAAGTCTGGA  AACGCGGAAG    1080

TCAGCGCCCT  GCACCATTAT  GTTCCGGATC  TGCATCGCAG  GATGCTGCTG  GCTACCCTGT    1140

GGAACACCTA  CATCTGTATT  AACGAAGCGC  TGGCATTGAC  CCTGAGTGAT  TTTTCTCTGG    1200

TCCCGCCGCA  TCCATACCGC  CAGTTGTTTA  CCCTCACAAC  GTTCCAGTAA  CCGGGCATGT    1260

TCATCATCAG  TAACCCGTAT  CGTGAGCATC  CTCTCTCGTT  TCATCGGTAT  CATTACCCCC    1320

ATGAACAGAA  ATTCCCCCTT  ACACGGAGGC  ATCAAGTGAC  CAAACAGGAA  AAAACCGCCC    1380

TTAACATGGC  CCGCTTTATC  AGAAGCCAGA  CATTAACGCT  TCTGGAGAAA  CTCAACGAGC    1440

TGGACGCGGA  TGAACAGGCA  GACATCTGTG  AATCGCTTCA  CGACCACGCT  GATGAGCTTT    1500

ACCGCAGCTG  CCTCGCGCGT  TTCGGTGATG  ACGGTGAAAA  CCTCTGACAC  ATGCAGCTCC    1560

CGGAGACGGT  CACAGCTTGT  CTGTAAGCGG  ATGCCGGGAG  CAGACAAGCC  CGTCAGGGCG    1620

CGTCAGCGGG  TGTTGGCGGG  TGTCGGGGCG  CAGCCATGAC  CCAGTCACGT  AGCGATAGCG    1680

GAGTGTATAC  TGGCTTAACT  ATGCGGCATC  AGAGCAGATT  GTACTGAGAG  TGCACCATAT    1740

GCGGTGTGAA  ATACCGCACA  GATGCGTAAG  GAGAAAATAC  CGCATCAGGC  GCTCTTCCGC    1800

TTCCTCGCTC  ACTGACTCGC  TGCGCTCGGT  CGTTCGGCTG  CGGCGAGCGG  TATCAGCTCA    1860
```

```
CTCAAAGGCG  GTAATACGGT  TATCCACAGA  ATCAGGGGAT  AACGCAGGAA  AGAACATGTG   1920

AGCAAAAGGC  CAGCAAAAGG  CCAGGAACCG  TAAAAAGGCC  GCGTTGCTGG  CGTTTTTCCA   1980

TAGGCTCCGC  CCCCCTGACG  AGCATCACAA  AAATCGACGC  TCAAGTCAGA  GGTGGCGAAA   2040

CCCGACAGGA  CTATAAAGAT  ACCAGGCGTT  TCCCCCTGGA  AGCTCCCTCG  TGCGCTCTCC   2100

TGTTCCGACC  CTGCCGCTTA  CCGGATACCT  GTCCGCCTTT  CTCCCTTCGG  GAAGCGTGGC   2160

GCTTTCTCAT  AGCTCACGCT  GTAGGTATCT  CAGTTCGGTG  TAGGTCGTTC  GCTCCAAGCT   2220

GGGCTGTGTG  CACGAACCCC  CCGTTCAGCC  CGACCGCTGC  GCCTTATCCG  GTAACTATCG   2280

TCTTGAGTCC  AACCCGGTAA  GACACGACTT  ATCGCCACTG  GCAGCAGCCA  CTGGTAACAG   2340

GATTAGCAGA  GCGAGGTATG  TAGGCGGTGC  TACAGAGTTC  TTGAAGTGGT  GGCCTAACTA   2400

CGGCTACACT  AGAAGGACAG  TATTTGGTAT  CTGCGCTCTG  CTGAAGCCAG  TTACCTTCGG   2460

AAAAAGAGTT  GGTAGCTCTT  GATCCGGCAA  ACAAACCACC  GCTGGTAGCG  GTGGTTTTTT   2520

TGTTTGCAAG  CAGCAGATTA  CGCGCAGAAA  AAAAGGATCT  CAAGAAGATC  CTTTGATCTT   2580

TTCTACGGGG  TCTGACGCTC  AGTGGAACGA  AAACTCACGT  TAAGGGATTT  GGTCATGAG    2640

ATTATCAAAA  AGGATCTTCA  CCTAGATCCT  TTTAAATTAA  AAATGAAGTT  TTAAATCAAT   2700

CTAAAGTATA  TATGAGTAAA  CTTGGTCTGA  CAGTTACCAA  TGCTTAATCA  GTGAGGCACC   2760

TATCTCAGCG  ATCTGTCTAT  TTCGTTCATC  CATAGTTGCC  TGACTCCCCG  TCGTGTAGAT   2820

AACTACGATA  CGGGAGGGCT  TACCATCTGG  CCCCAGTGCT  GCAATGATAC  CGCGAGACCC   2880

ACGCTCACCG  GCTCCAGATT  TATCAGCAAT  AAACCAGCCA  GCCGGAAGGG  CCGAGCGCAG   2940

AAGTGGTCCT  GCAACTTTAT  CCGCCTCCAT  CCAGTCTATT  AATTGTTGCC  GGGAAGCTAG   3000

AGTAAGTAGT  TCGCCAGTTA  ATAGTTTGCG  CAACGTTGTT  GCCATTGCTG  CAGGCATCGT   3060

GGTGTCACGC  TCGTCGTTTG  GTATGGCTTC  ATTCAGCTCC  GGTTCCCAAC  GATCAAGGCG   3120

AGTTACATGA  TCCCCCATGT  TGTGCAAAAA  AGCGGTTAGC  TCCTTCGGTC  CTCCGATCGT   3180

TGTCAGAAGT  AAGTTGGCCG  CAGTGTTATC  ACTCATGGTT  ATGGCAGCAC  TGCATAATTC   3240

TCTTACTGTC  ATGCCATCCG  TAAGATGCTT  TTCTGTGACT  GGTGAGTACT  CAACCAAGTC   3300

ATTCTGAGAA  TAGTGTATGC  GGCGACCGAG  TTGCTCTTGC  CCGGCGTCAA  CACGGGATAA   3360

TACCGCGCCA  CATAGCAGAA  CTTTAAAAGT  GCTCATCATT  GGAAAACGTT  CTTCGGGGCG   3420

AAAACTCTCA  AGGATCTTAC  CGCTGTTGAG  ATCCAGTTCG  ATGTAACCCA  CTCGTGCACC   3480

CAACTGATCT  TCAGCATCTT  TTACTTTCAC  CAGCGTTTCT  GGGTGAGCAA  AAACAGGAAG   3540

GCAAAATGCC  GCAAAAAAGG  GAATAAGGGC  GACACGGAAA  TGTTGAATAC  TCATACTCTT   3600

CCTTTTTCAA  TATTATTGAA  GCATTATCA   GGGTTATTGT  CTCATGAGCG  GATACATATT   3660

TGAATGTATT  TAGAAAAATA  AACAAATAGG  GGTTCCGCGC  ACATTTCCCC  GAAAAGTGCC   3720

ACCTGACGTC  TAAGAAACCA  TTATTATCAT  GACATTAACC  TATAAAAATA  GGCGTATCAC   3780

GAGGCCCTTT  CGTCTTCAAG  AATTAATTCG  GTCGAAAAAA  GAAAAGGAGA  GGGCCAAGAG   3840

GGAGGGCATT  GGTGACTATT  GAGCACGTGA  GTATACGTGA  TTAAGCACAC  AAAGGCAGCT   3900

TGGAGTATGT  CTGTTATTAA  TTTCACAGGT  AGTTCTGGTC  CATTGGTGAA  AGTTTGCGGC   3960

TTGCAGAGCA  CAGAGGCCGC  AGAATGTGCT  CTAGATTCCG  ATGCTGACTT  GCTGGGTATT   4020

ATATGTGTGC  CCAATAGAAA  GAGAACAATT  GACCCGGTTA  TTGCAAGGAA  AATTTCAAGT   4080

CTTGTAAAAG  CATATAAAAA  TAGTTCAGGC  ACTCCGAAAT  ACTTGGTTGG  CGTGTTTCGT   4140

AATCAACCTA  AGGAGGATGT  TTTGGCTCTG  GTCAATGATT  ACGGCATTGA  TATCGTCCAA   4200

CTGCATGGAG  ATGAGTCGTG  GCAAGAATAC  CAAGAGTTCC  TCGGTTTGCC  AGTTATTAAA   4260
```

-continued

| | | | | | | |
|---|---|---|---|---|---|---|
| AGACTCGTAT | TTCCAAAAGA | CTGCAACATA | CTACTCAGTG | CAGCTTCACA | GAAACCTCAT | 4320 |
| TCGTTTATTC | CCTTGTTTGA | TTCAGAAGCA | GGTGGGACAG | GTGAACTTTT | GGATTGGAAC | 4380 |
| TCGATTTCTG | ACTGGGTTGG | AAGGCAAGAG | AGCCCCGAAA | GCTTACATTT | TATGTTAGCT | 4440 |
| GGTGGACTGA | CGCCAGAAAA | TGTTGGTGAT | GCGCTTAGAT | TAAATGGCGT | TATTGGTGTT | 4500 |
| GATGTAAGCG | GAGGTGTGGA | GACAAATGGT | GTAAAGACT | CTAACAAAAT | AGCAAATTTC | 4560 |
| GTCAAAAATG | CTAAGAAATA | GGTTATTACT | GAGTAGTATT | TATTTAAGTA | TTGTTTGTGC | 4620 |
| ACTTGCCTGC | AGCTTCTCAA | TGATATTCGA | ATACGCTTTG | AGGAGATACA | GCCTAATATC | 4680 |
| CGACAAACTG | TTTTACAGAT | TTACGATCGT | ACTTGTTACC | CATCATTGAA | TTTTGAACAT | 4740 |
| CCGAACCTGG | GAGTTTTCCC | TGAAACAGAT | AGTATATTTG | AACCTGTATA | ATAATATATA | 4800 |
| GTCTAGCGCT | TTACGGAAGA | CAATGTATGT | ATTTCGGTTC | CTGGAGAAAC | TATTGCATCT | 4860 |
| ATTGCATAGG | TAATCTTGCA | CGTCGCATCC | CCGGTTCATT | TTCTGCGTTT | CCATCTTGCA | 4920 |
| CTTCAATAGC | ATATCTTTGT | TAACGAAGCA | TCTGTGCTTC | ATTTGTAGA | ACAAAAATGC | 4980 |
| AACGCGAGAG | CGCTAATTTT | TCAAACAAAG | AATCTGAGCT | GCATTTTTAC | AGAACAGAAA | 5040 |
| TGCAACGCGA | AAGCGCTATT | TTACCAACGA | AGAATCTGTG | CTTCATTTTT | GTAAACAAA | 5100 |
| AATGCAACGC | GAGAGCGCTA | ATTTTTCAAA | CAAGAATCT | GAGCTGCATT | TTACAGAAC | 5160 |
| AGAAATGCAA | CGCGAGAGCG | CTATTTTACC | AACAAAGAAT | CTATACTTCT | TTTTGTTCT | 5220 |
| ACAAAAATGC | ATCCCGAGAG | CGCTATTTTT | CTAACAAAGC | ATCTTAGATT | ACTTTTTTC | 5280 |
| TCCTTTGTGC | GCTCTATAAT | GCAGTCTCTT | GATAACTTTT | TGCACTGTAG | GTCCGTTAAG | 5340 |
| GTTAGAAGAA | GGCTACTTTG | GTGTCTATTT | TCTCTTCCAT | AAAAAAAGCC | TGACTCCACT | 5400 |
| TCCCGCGTTT | ACTGATTACT | AGCGAAGCTG | CGGGTGCATT | TTTTCAAGAT | AAAGGCATCC | 5460 |
| CCGATTATAT | TCTATACCGA | TGTGGATTGC | GCATACTTTG | TGAACAGAAA | GTGATAGCGT | 5520 |
| TGATGATTCT | TCATTGGTCA | GAAAATTATG | AACGGTTTCT | TCTATTTTGT | CTCTATATAC | 5580 |
| TACGTATAGG | AAATGTTTAC | ATTTTCGTAT | TGTTTTCGAT | TCACTCTATG | AATAGTTCTT | 5640 |
| ACTACAATTT | TTTTGTCTAA | AGAGTAATAC | TAGAGATAAA | CATAAAAAAT | GTAGAGGTCG | 5700 |
| AGTTTAGATG | CAAGTTCAAG | GAGCGAAAGG | TGGATGGGTA | GGTTATATAG | GGATATAGCA | 5760 |
| CAGAGATATA | TAGCAAAGAG | ATACTTTGA | GCAATGTTTG | TGGAAGCGGT | ATTCGCAATA | 5820 |
| TTTTAGTAGC | TCGTTACAGT | CCGGTGCGTT | TTTGGTTTTT | TGAAAGTGCG | TCTTCAGAGC | 5880 |
| GCTTTTGGTT | TTCAAAAGCG | CTCTGAAGTT | CCTATACTTT | CTAGAGAATA | GGAACTTCGG | 5940 |
| AATAGGAACT | TCAAAGCGTT | TCCGAAAACG | AGCGCTTCCG | AAAATGCAAC | GCGAGCTGCG | 6000 |
| CACATACAGC | TCACTGTTCA | CGTCGCACCT | ATATCTGCGT | GTTGCCTGTA | TATATATATA | 6060 |
| CATGAGAAGA | ACGGCATAGT | GCGTGTTTAT | GCTTAAATGC | GTACTTATAT | GCGTCTATTT | 6120 |
| ATGTAGGATG | AAAGGTAGTC | TAGTACCTCC | TGTGATATTA | TCCCATTCCA | TGCGGGGTAT | 6180 |
| CGTATGCTTC | CTTCAGCACT | ACCCTTTAGC | TGTTCTATAT | GCTGCCACTC | CTCAATTGGA | 6240 |
| TTAGTCTCAT | CCTTCAATGC | TATCATTTCC | TTTGATATTG | GATCATATGC | ATAGTACCGA | 6300 |
| GAAACTAGTG | CGAAGTAGTG | ATCAGGTATT | GCTGTTATCT | GATGAGTATA | CGTTGTCCTG | 6360 |
| GCCACGGCAG | AAGCACGCTT | ATCGCTCCAA | TTTCCCACAA | CATTAGTCAA | CTCCGTTAGG | 6420 |
| CCCTTCATTG | AAAGAAATGA | GGTCATCAAA | TGTCTTCCAA | TGTGAGATTT | TGGGCCATTT | 6480 |
| TTTATAGCAA | AGATTGAATA | AGGCGCATTT | TTCTTCAAGG | GGGGGGGGG | GGGGGGGGG | 6540 |
| TTACTTAACC | AATCTACATA | GATACTATAT | TTAACATTCA | ACATAATAAT | AAATATTTG | 6600 |
| GGATAAATAA | GTGAAACCAT | TTTAGAGCCC | CTAGGGCTTA | CAAAAGAAT | CATAAAGAT | 6660 |

-continued

| | | | | | | |
|---|---|---|---|---|---|---|
| CCATATTTAT | AGTTTTAAGA | TTAAGAATAA | TAGTTACAAT | AGGTAGCAAA | CCATACATTC | 6720 |
| AACAATAAAT | ATAAAATTTA | AATATTTAAA | TAAATAGAAG | GGGTACGAGG | GGGCCATGGA | 6780 |
| CGAGCTCTAT | TACTGAAGGT | ATTCCTCAGG | GATCTCTTCG | AAGTCGCCGT | CGTTATGAGA | 6840 |
| CTGCGGTTTC | GGGGTACCTT | CGCCAGTAAC | GCACTGGTTC | TTTTCACCGT | CGGATCCAAG | 6900 |
| GATGCATTTG | TTACCCTGGC | CGCAAACGTT | AGATCCTTCG | CACAGGCACA | GGTTCTGACC | 6960 |
| AGATTCAGTG | CAGTCAGTAT | ACGTAAGTCT | TTTATCCAAA | GGTACCCCTT | CTTCTTTAGC | 7020 |
| AGCAATGCTG | GCAATAGTAG | TATTTATAAA | CAATAACCCG | TTATTTGTGC | TGTTGGAAAA | 7080 |
| TGGCAAAACA | GCAACATCGA | AATCCCCTTC | TAAATCTGAG | TAACCGATGA | CAGCTTCAGC | 7140 |
| CGGAATTTGT | GCCGTTTCAT | CTTCTGTTGT | AGTGTTGACT | GGAGCAGCTA | ATGCGGAGGA | 7200 |
| TGCTGCGAAT | AAAACTGCAG | TAAAAATTGA | AGGAAATCTC | ATCGTGAGGT | CGAGCTTGGT | 7260 |
| GTATTACGAT | ATAGTTAATA | GTTGATAGTT | GATTGTATGC | TTTTGTAGC | TTGATATTCT | 7320 |
| ATTTACCAAG | AAGAAACAAG | AAGTGATAAA | AACAACAAGA | GAGCAGTAGT | AAGAGTATTT | 7380 |
| CAGTGTGAAA | AAAGTCGCTA | CTGGCACTCT | ATTTATATGT | GATAGGCATG | CTATAGCTTT | 7440 |
| ACCAAAAAGT | GAACCCCATT | TCTATGCTCT | CCTCTGCCTT | TTTTTTTTT | TTTTTTTCA | 7500 |
| TTCTCTCAAT | CTGAAATTCT | CTTATTTCTC | CAACTTATAA | GTTGGAGATG | CCCGGTGTTC | 7560 |
| CGGCAGAGGA | GATCAGTCTC | GTGAAGTGGA | TGGTTTCCCG | CCTGCGGGCA | AAACGTCATA | 7620 |
| ACATTTTTAT | GAGCGAAAGC | CGTTAATGAA | GACAAAATCC | CTTAATTAAA | ACATTAGAAT | 7680 |
| GGTGATTAGA | AAGGCAGGAT | TAATCAGTTA | CACAGGCTGT | AACCGGAGAG | ACGGATCATA | 7740 |
| AGGCAATTTT | TAGATAAGAC | TGGTTAGAGT | TCTTGGCATC | AGAAAATTTG | AGAAACGATT | 7800 |
| TTTCCGTTTG | TTTGCCCCTA | CGTTTTGCCC | CTTTGATCAA | ACTATCAGTT | AAGATATTAA | 7860 |
| TTTTTTTGAG | AAAACGATTC | TTTGATTAGT | CTCTTCAAAC | AAACAATGAG | CTCTGAAGAC | 7920 |
| GAATTGGGAA | GTATCGGTAC | TGTGTTTCCC | GGAAGTCCCA | TAGATAAGAG | CATTGGGAGT | 7980 |
| ATTCTCCACA | ATTTGATGAA | GAAGTGGAGA | CTTTGCTGGA | AGATAGCTTC | ACGTGGAACA | 8040 |
| TTCCTGACTG | GAACGAGTTA | ACAAACCCGA | AATACAATTC | GCCCAGGTTT | AGAATTGGTG | 8100 |
| ATTTCGAATG | GGACATTCTA | TTATTCCCTC | AGGGAAACCA | TAATAAAGGT | GTTGCGGTAT | 8160 |
| ATCTGGAACC | TCATCCGGAA | GAAAAATTAG | ATGAGACTAC | GGGAGAGATG | GTGCCAGTTG | 8220 |
| ATCCGGACTG | GTATTGTTGT | GCTCAGTTTG | CCATTGGTAT | ATCTAGACCT | GGTAATGGTG | 8280 |
| ACACCATCAA | TTTAATTAAC | AAATCGCATC | ACCGATTCAA | CGCTCTAGAT | ACAGACTGGG | 8340 |
| GATTTGCAAA | TTTGATAGAT | TTGAACAACT | TGAAACATCC | CTCAAAAGGA | AGACCGCTTT | 8400 |
| CGTTCTTAAA | CGAAGGGACC | TTGAACATAA | CAGCGTATGT | GCGCATATTG | AAGGATCTCT | 8460 |
| ACTTGTCAAA | TACCTTTAAA | TCTTATCAAT | A | | | 8491 |